(12) United States Patent
Karim et al.

(10) Patent No.: US 6,605,739 B1
(45) Date of Patent: *Aug. 12, 2003

(54) METHOD FOR PRODUCING VINYL ACETATE MONOMER FROM ETHANE OR ETHYLENE OXIDATION

(75) Inventors: Khalid Karim, Manchester (GB); Alaa E. M. Adris, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 10/031,808

(22) PCT Filed: May 9, 2000

(86) PCT No.: PCT/EP00/04234

§ 371 (c)(1),
(2), (4) Date: Nov. 13, 2001

(87) PCT Pub. No.: WO00/69802

PCT Pub. Date: Nov. 23, 2000

(51) Int. Cl.[7] ....................... C07C 69/15; C07C 67/055; C07C 51/215; C07C 53/08
(52) U.S. Cl. ....................... 560/245; 560/261; 562/549; 562/607
(58) Field of Search ................... 560/245, 261; 562/549, 607

(56) References Cited

U.S. PATENT DOCUMENTS

| | | | |
|---|---|---|---|
| 3,190,912 A | 6/1965 | Robinson | 260/497 |
| 3,637,819 A | 1/1972 | Sennewald et al. | 260/497 |
| 3,792,087 A | 2/1974 | McClain et al. | 260/533 |
| 3,970,697 A | 7/1976 | Scheben et al. | 260/533 |
| 4,188,490 A | 2/1980 | Hinnenkamp et al. | 560/245 |
| 4,370,492 A | 1/1983 | Wunder et al. | 560/245 |
| 4,902,823 A | 2/1990 | Wunder et al. | 560/245 |
| 5,185,308 A | 2/1993 | Bartley et al. | 502/170 |

FOREIGN PATENT DOCUMENTS

| | | | |
|---|---|---|---|
| DE | 19630832 A | 2/1998 | |
| WO | WO98/05620 A1 | 2/1998 | 53/8 |
| WO | WO99/13980 A | 3/1999 | |

*Primary Examiner*—Brian Davis
(74) *Attorney, Agent, or Firm*—Kramer Levin Naftalis & Frankel LLP

(57) ABSTRACT

Methods for the catalytic production of vinyl acetate monomer from ethane, ethylene or an ethanelethylene mixture using a first catalyst containing MoVNbPd, MoVLaPdbX (where X is Al, Ga, Ge or Si) or MoVNbX (where X is P, B, Hf, Te, As or mixtures thereof) in the first step of oxidation and using a conventional VAM catalyst for the second step. The method produces high yields to acetic acid and vinyl acetate without the coproduction of carbon monoxide. Furthermore, the ethylene and acetic acid produced in the first step may be utilized in the second step for VAM production.

15 Claims, 2 Drawing Sheets

METHOD FOR PRODUCING VINYL ACETATE MONOMER FROM ETHANE OR ETHYLENE OXIDATION

The present invention relates to a process for the production of vinyl acetate monomer according to the preamble of claims 1 and 15.

The invention relates to improved integrated methods of making vinyl acetate monomers from ethane or ethylene using metal oxide catalysts.

Several publications are referenced in this application. These references describe the state of the art to which this invention pertains.

The utilization of lower alkanes ($C_1$–$C_4$) as feed stock to produce value added petrochemicals is an industrially desired process. Lower alkanes are low cost and environmentally acceptable because of their low chemical reactivity. There are only a few commercially available chemical catalytic processes, which utilize lower alkanes as a feed, such as butane to maleic anhydride.

Vinyl acetate monomer (VAM) is a well-known industrial chemical. The production of VAM from ethylene, oxygen and acetic acid using conventional VAM catalysts is known in the art. VAM is typically used as a raw material for vinyl resins such as polyvinyl acetate. VAM was previously primarily manufactured from the vapor phase reaction of ethylene, acetic acid and oxygen with a zinc acetate catalyst.

More recently, VAM has been produced from the vapor-phase reaction of ethylene, acetic acid and oxygen, with a palladium catalyst. For example, VAM may be made from ethylene wherein the first step involves reacting the ethylene to form acetic acid, followed by a second step of reacting a mixture of the acetic acid and ethylene to form vinyl acetate.

Numerous methods are known for the catalytic oxidation of ethylene to acetic acid. See, for example, U.S. Pat. Nos. 3,792,087 and 3,970,697. Similarly, numerous methods are known for the catalytic production of vinyl acetate by reacting ethylene with acetic acid and oxygen in the gaseous phase. See, U.S. Pat. Nos. 3,190,912; 3,637,819; 3,650,896; 4,370,492; 5,185,308; and 4,902,823.

PCT Patent Publication WO 98/05620 describes the production of acetic acid and/or vinyl acetate from ethylene (or ethane) using a first catalyst active for the oxidation of ethylene to acetic acid and/or active for the oxidation of ethane to acetic acid, ethylene and carbon monoxide, and a second catalyst active for the production of vinyl acetate. The patent also describes an additional necessary step for conversion of carbon monoxide to carbon dioxide. This is because carbon monoxide is poisonous to the VAM catalyst.

U.S. Pat. No. 4,188,490 relates to a catalytic oxidation process for the production of mixtures of acetic acid and vinyl acetate comprising the step of contacting a feed mixture containing ethylene, oxygen and water (as steam) with a catalyst composition to provide a mixture of acetic acid and vinyl acetate. The catalyst system comprises a palladium metal on a zinc oxide support treated in the presence of a sulfur modifier. The method requires the subsequent step of fractional distillation to separate the acetic acid from the vinyl acetate. Alternatively, the acetic acid contained in the product mixture is converted in situ to an alkali metal salt such as sodium acetate. The method also requires the step of treating the catalyst with the sulfur modifier by, for example, flowing moist air containing $SO_2$ over the catalyst at 200° C. for about one hour.

WO 99/13980 discloses an oxide catalyst comprising the elements Mo, V and Nb with small amounts of phosphorus, boron, hafnium, Te and/or As. The modified catalyst provides both higher selectivity and yield of acetic acid in the low temperature oxidation of ethane with molecular oxygen-containing gas. A process for the higher selective production of acetic acid by the catalytic oxidation of ethane wish oxygen, in the presence of the improved catalyst.

WO 98/05620 describes acetic acid and/or vinyl acetate which are produced by an integrated process which comprises the steps: (a) contacting in a first reaction zone a gaseous feedstock comprising ethylene and/or ethane and optionally steam with a molecular oxygen-containing gas in the presence of a catalyst active for the oxidation of ethylene to acetic acid and/or ethane to acetic acid and ethylene to produce a first product stream comprising acetic acid, water and ethylene (either as unreacted ethylene and/or as co-produced ethylene) and optionally also ethane, carbon monoxide, carbon dioxide and/or nitrogen; (b) contacting in a second reaction the presence or absence of additional ethylene and/or acetic acid at least a portion of the first gaseous product stream comprising at least acetic acid and ethylene and optionally also one or more of water, ethane, carbon monoxide, carbon dioxide and/or nitrogen with a molecular oxygen-containing gas in the presence of a catalyst active for the production of vinyl acetate to produce a second product stream comprising vinyl acetate, water, acetic acid and optionally ethylene; (c) separating the product stream from step (b) by distillation into an overhead azeotrope fraction comprising vinyl acetate and water and a base fraction comprising acetic acid, (d) either (i) recovering acetic acid from the base fraction separated in step (c) and optionally recycling the azeotrope fraction separated in step (c) after partial or complete separation of the water therefrom to step (c) or (ii) recovering vinyl acetate from the azeotrope fraction separated in step (c) and optionally recycling the base fraction separated in step (c) to step (b), or (iii) recovering acetic acid from the base fraction separated in step (c) and recovering vinyl acetate from the overhead azeotrope fraction recovered in step (c).

DE-A-19630832 relates to a process for the selective preparation of acetic acid from a gaseous feed comprising ethane, ethylene or mixtures thereof plus oxygen at elevated temperature, which comprises bringing the gaseous feed into contact with a catalyst comprising the elements Mo, Pd, X and Y in gram atom ratios a:b:c:d in combination with oxygen where the symbols X and Y have the following meanings; X is one or more elements selected from the group consisting of: Cr, Mn, Nb, Ta, Ti, V, Te and/or W, in particular Nb, v and W; Y is one or more elements selected from the group consisting of: B, Al, Ga, In, Pt, Zn, Cd, Bi, Ce, Co, Cu, Rh, Ir, Au, Ag, Fe, Ru, Os, K, Rb, Co, Mg, Ca, Sr, Ba, Zr, Hf, Ni, P, Pb, Sb, Si, Sn, Tl and U, in particular Ca, Sb, Te, and Li. This invention further provides a catalyst for the selective preparation of acetic acid comprising the elements Mo, Pd, X and Y in the gram atom ratios a:b:c:d in combination with oxygen.

Several methods for producing vinyl acetate from ethylene result in the production of carbon monoxide. The production of carbon monoxide is disadvantageous because it is poisonous to the second stage catalyst. Moreover, carbon monoxide is also a less desirable by-product due to environmental law constraints. In order to avoid this problem, it is necessary to introduce another catalytic reactor for the total oxidation of CO to $CO_2$. This can add significant costs to the catalytic process.

Accordingly, it would be desirable to provide an improved method for the selective production of vinyl acetate monomer from ethane without the production of carbon monoxide.

It is an object of the invention to overcome the above-identified deficiencies.

It is another object of the invention to provide an improved catalytic method for the production of vinyl acetate.

It is a further object of the invention to provide an improved catalytic method for the oxidation of ethylene to produce vinyl acetate.

It is a further object of the invention to provide an improved catalytic method for the oxidation of ethane to produce vinyl acetate.

It is a still further object of the invention to provide an improved catalytic method for the oxidation of ethane, ethylene or a mixture of ethane and ethylene to produce vinyl acetate without the production of carbon monoxide as a by-product.

It is yet another object of the invention to provide an improved catalytic method for the single stage oxidation of ethane or ethylene or mixtures thereof to vinyl acetate.

The foregoing and other objects and advantages of the invention will be set forth in or be apparent from the following description.

The process of the present invention is defined in the characterizing portion of claims 1 and 15.

According to the present invention, vinyl acetate is produced catalytically from ethane feed stocks. Another aspect of the invention relates to the production of vinyl acetate from ethylene. The catalysts suitable for use in the methods of the invention are active and selective to the desired end product, vinyl acetate. The catalytic process for the production of VAM from ethane involves two steps. In the first step, a catalyst (the "first catalyst") is used to provide the function of activation of ethane to ethylene and acetic acid. In the second step, ethylene and acetic acid are further oxidized to VAM in the presence of a conventional VAM catalyst (the "second catalyst"). Another preferred embodiment relates to a method of forming a stoichiometric mixture of ethylene and acetic acid using the first catalyst, which mixture can be directly fed into a vinyl acetate reactor containing the VAM catalyst without adjustments. Yet another preferred embodiment relates to a catalytic method wherein ethylene or ethane is converted to vinyl acetate in a single stage reactor.

Advantageously, the preferred catalytic methods of the invention do not produce carbon monoxide. This is advantageous because carbon monoxide is not environmentally friendly and can have a significant impact on down stream separation costs, as well as on the poisoning of the VAM catalyst.

Other objects as well as aspects, features and advantages of the present invention will become apparent from a study of the present specification, including the claims, figures and specific examples.

Figure 1:
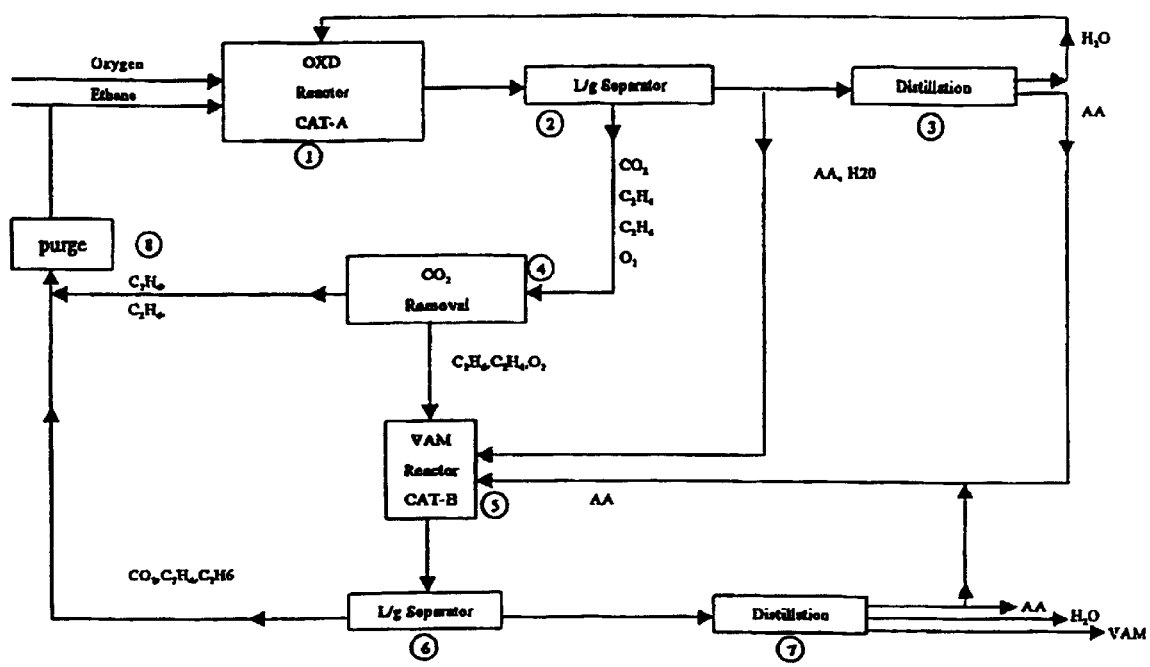
FIG. 1 is a schematical representation of a ethane to VAM reaction scheme according to one embodiment of the invention.

The invention relates to novel methods of producing vinyl acetate. In the first step, the first catalyst is used which provides the dual functions of (a) activation of ethane (or ethane/ethylene) to acetic acid and ethylene and (b) ethylene to acetic acid. In the second step, vinyl acetate is formed through further oxidation of ethylene with acetic acid in the presence of a second catalyst, the VAM catalyst. According to one preferred embodiment, the catalysts of the invention can also be used to provide an optimal feed to a vinyl acetate reactor. That is, catalytically oxidizing ethane (or ethylene/ethane) to form a mixture containing the optimal stoichiometric mixture of ethylene and acetic acid for use as a feed to a vinyl acetate reactor containing the conventional VAM catalyst, such as a Pd/Al catalyst.

The catalyst system suitable for the first step of the present invention (the first catalyst) can be formed from compositions including a catalyst (a) of the formula $Mo_aV_bNb_cPd_d$, wherein:

a is 1 to 5;

b is 0 to 0.5;

c is 0.01 to 0.5; and d is >0 to 0.2.

The numerical values of a, b, c and d represent the relative gram-atom ratios of the elements Mo, V, Nb and Pd, respectively, in the catalyst. The elements are preferably present in combination with oxygen in the form of various oxides.

Another catalyst system, catalyst (b), has a composition comprising the elements Mo, V, Pd, Nb, La, and X where X is Al, Ga, Si, or Ge) in the form of oxides in the ratio $Mo_aV_bLa_cPd_dNb_eX_f$ wherein:

a is 1;

b is 0.01 to 0.9;

c is >0 to 0.2;

d is >0 to 0.2.

e is >0 to 0.2; and f is >0 to 0.3.

The numerical values of a, b, c, d, e and f represent the relative gram-atom ratios of the elements Mo, V, Pd, La, Nb and X, respectively, in the catalyst. The elements are preferably present in combination with oxygen in the form of various oxides.

Another catalyst system, catalyst (c), suitable for the invention is formed from a calcined composition of $MO_aV_bNb_cX_d$, wherein:

X is at least one promoter element selected from the group consisting of: P, B, Hf, Te, and As;

a is 1 to 5;

b is 1;

c is 0.01 to 0.5; and d is 0 to 0.1.

The numerical values of a, b, c and d represent the relative gram-atom ratios of the elements Mo, V, Nb and X, respectively, in the catalyst. The elements are preferably present in combination with oxygen in the form of various oxides.

The first catalyst (catalysts (a) or (b) or (c) or mixtures thereof) and methods of making the first catalyst are set forth in U.S. Pat. No. 6,043,597, filed Sep. 17, 1997, entitled "Catalysts for the Oxidation of Ethane to Acetic Acid, Processes of Making the Same and Processes of Using the Same"; U.S. Pat. No. 6,030,292, filed Dec. 24, 1997, entitled "Catalyst for Producing Acetic Acid from Ethane Oxidation, Processes of Making the Same and Methods of Using the Same" and U.S. Pat. No. 6,060,421, filed Dec. 23, 1998, entitled "Catalysts for the Oxidation of Ethane to Acetic Acid, Methods of Making and Using the Same".

One broad aspect of the invention relates to the production of vinyl acetate from ethane, ethylene or mixtures of ethane and ethylene. The method utilizes a first catalyst ((a) or (b) or (c) or mixtures thereof) providing the functions of activation of ethane to acetic acid and ethylene and further oxidation of ethylene with acetic acid to vinyl acetate using a conventional VAM catalyst such as a Pd/Al catalyst. Overall, the recycled yield for vinyl acetate can be greater than 95%.

Advantageously, the methods of the invention produce vinyl acetate with zero (or nondetectable) or insignificant production of carbon monoxide. Preferably, less than 0.1 wt % carbon monoxide is produced as an end product using the invention, more preferably less than 0.01% and most preferred no detectable carbon monoxide is produced. Accordingly, one preferred aspect of the invention relates to a method which employs a catalyst designed in such way that it does not produce any CO, which saves the treatment step of converting CO to $CO_2$.

One embodiment of the invention comprises reacting ethane with oxygen and water (e.g. steam) in the presence of a first catalyst ((a) or (b) or (c) or mixtures thereof) to form a mixture containing ethylene and acetic acid which is then reacted to form vinyl acetate.

The raw material used as the source for the ethane or ethylene/ethane can be a gas stream, which preferably contains at least five volume percent of ethane/ethylene. The gas can also contain minor amounts of the $C_3$–$C_4$ alkanes and alkenes, preferably less than five volume percent of each. The gas stream can also contain major amounts, preferably more than five volume percent, of nitrogen, carbon dioxide, and water in the form of steam.

The reaction mixture useful in carrying out the process is generally from 5 to 50 moles % of ethane, 5 to 50 moles % of molecular oxygen either as pure oxygen or in the form of air, and optionally 2 to 50 moles t of water in the form of steam. The amount of oxygen present may be a stoichiometric amount, or lower, of the hydrocarbons in the feed. Other gases may be used as reaction diluents or heat moderators such as helium, nitrogen, and carbon dioxide.

The gaseous components of the reaction mixture are preferably uniformly admixed prior to being introduced into the reaction zone. The components may be preheated, individually or after being mixed, prior to being introduced into the reaction zone.

The first reaction zone, containing the first catalyst ((a) Pr (b) or (c) or mixtures thereof), generally has a pressure of from 1 to 34 bar (15 to 500 psi), preferably from 10 to 24 bar (150 to 350 psi); a temperature of from about 100° C. to about 450° C. preferably from 200° C. to 350° C. more preferably from 250° C. to 300° C.; a contact time between the reaction mixture and the catalyst of from about 2 seconds to about 100 seconds, preferably from 5 seconds to 30 seconds; and a space hourly velocity of from about 50 to about 50,000 $h^{-1}$, preferably from 100 to 10,000 $h^{-1}$ and most preferably from 200 to 3,000 $h^{-1}$.

According to one preferred embodiment, the process occurs in two stages. In the first stage, a mixture comprising ethane or ethylene, oxygen or a compound capable of providing oxygen and water (e.g., steam) is reacted to form a mixture containing ethylene, acetic acid, oxygen and water (e.g., steam). The product mixture of the first stage is then fed into the second stage and reacted to produce vinyl acetate.

The feed from the first stage may be adjusted prior to being introduced into the second stage. For example, the oxygen, ethylene and acetic acid concentration may be adjusted to optimize the catalytic reaction. Preferably, the first stage of the process produces a stoichiometric composition of acetic acid and ethylene as a feed for the second stage. According to one particularly preferred embodiment, adjustments of the feed for the second reactor are not required as the mixture produced in the first stage can be directly fed into the second stage. Thus, a dual-function catalyst can be used in the first stage to provide the feed stock for the second stage, which may contain a conventional Pd/Al VAM catalyst or any catalyst suitable for converting the feed stock of acetic acid and ethylene to VAM.

Therefore, using the present invention, VAM can also be directly produced from only ethane, oxygen and water without additional components since the outlet of the first reactor may be optimized to contain a stoichiometric mixture of acetic acid, ethylene and oxygen which is the feed mixture for the second reactor. Preferably, the temperature and pressure of the feed from the first stage are also not adjusted prior to the second stage.

According to one embodiment, the output from either the first or second stage is recycled into the same or an earlier stage. For example, the output from stage 1 may be recycled into stage 1 or the output from stage 2 may be recycled into stage 1 and/or stage 2.

According to another embodiment, the reaction zone comprises multiple stages of bilayered catalyst consisting of layers of a first catalyst ((a) or (b) or (c) or mixtures thereof) according to the invention and a second conventional vinyl acetate catalyst. In this manner, the first catalyst converts ethane to a mixture of acetic acid and ethylene, preferably to an optimal mixture, and the second catalyst converts the ethylene/acetic acid to vinyl acetate in a single reaction zone.

Accordingly, one preferred embodiment relates to a process carried out in a single stage with all the reactants being supplied as a single feed with unreacted initial reactants being recycled. However, multiple stage addition of oxygen to the reactor with an intermediate hydrocarbon feed can also be used. This may improve productivity to vinyl acetate and avoid potentially hazardous conditions.

Figure 2:
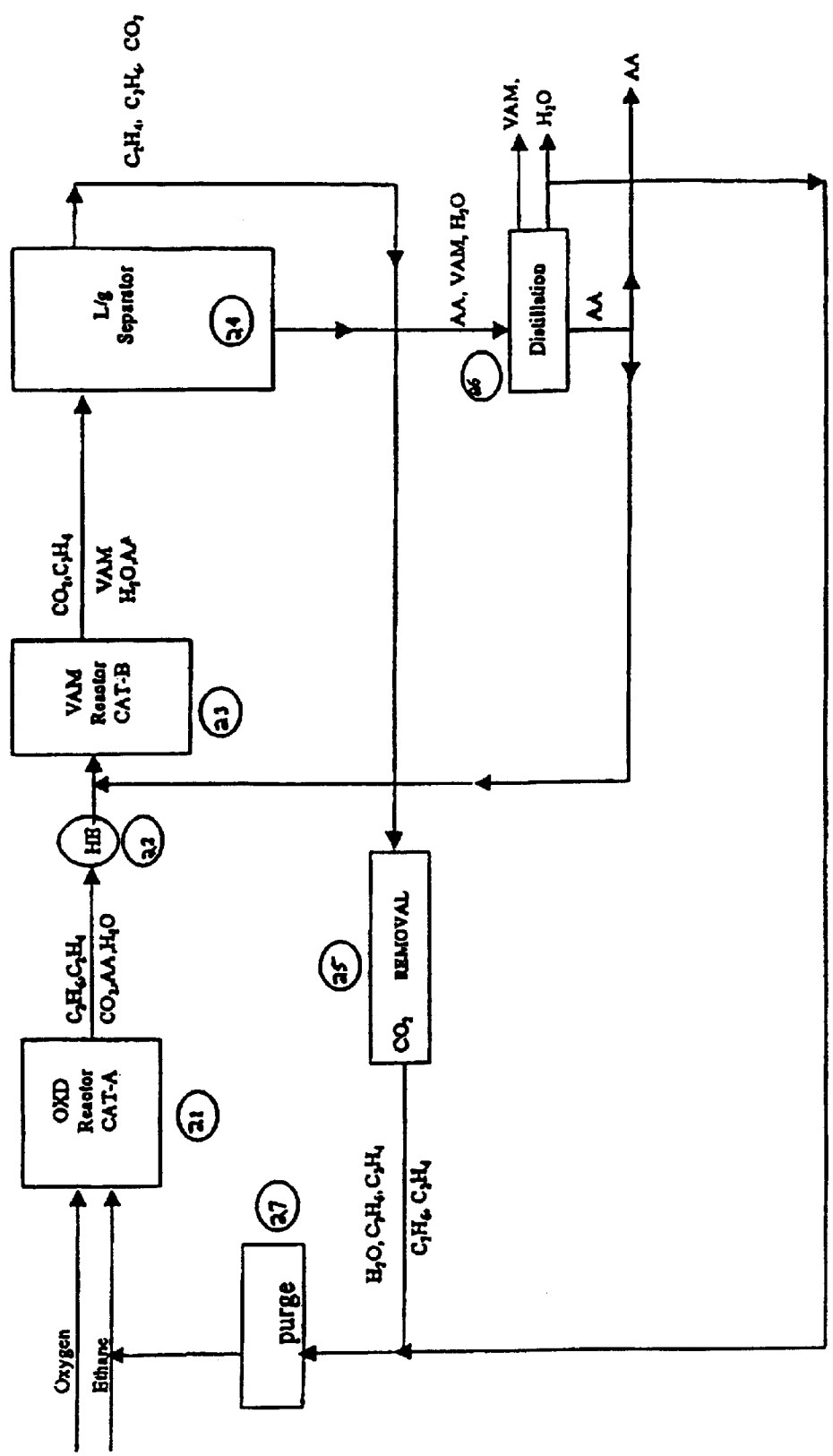
FIG. 2 is a schematical representation of a ethane to VAM reaction scheme according to another embodiment of the invention.

Two possible integrated schemes using the first catalyst and the second VAM catalyst for direct production of VAM from ethane or ethane/ethylene mixtures without producing carbon monoxide are shown in FIGS. 1 and 2.

FIG. 1 is schematical representation of one reaction scheme A according to one embodiment of the invention. The partial oxidation reactor 1 containing the first catalyst (CAT-A) converts fresh and recycled ethane or ethane/ethylene with oxygen into ethylene, acetic acid and carbon dioxide. An optimum amount of water from distillation reactor 3 is also introduced to partial oxidation reactor 1 in order to increase the acetic acid selectivity. The effluent from partial oxidation reactor 1 enters a gas/liquid separation unit 2. The gas stream from gas/liquid separation unit 2 is recycled to partial oxidation reactor 1 or goes to carbon dioxide absorption unit 4, where $CO_2$ is removed. The liquid stream from gas/liquid separation unit 2 goes to distillation unit 3, where acetic acid is separated from water or the liquid stream from gas/liquid separation unit 2 can directly go to VAM reactor 5 containing a conventional VAM catalyst (CAT-B). The treated gases consisting of ethane, ethylene and oxygen and the liquid stream consisting of acetic acid or acetic acid and water are fed to VAM reactor 5 to produce VAM, $CO_2$ and unreacted ethane, ethylene and acetic acid. The effluent of VAM reactor 5 is then fed to gas liquid separation unit 6 where gases including ethane, ethylene and $CO_2$ are separated, partially purged to control the build up of non reacting species in purge unit 8 and recycled back to partial oxidation reactor 1. The liquids are sent to distillation unit 7 for recovery of VAM. Acetic acid or unreacted acetic acid is recycled back to VAM reactor 5.

FIG. 2 is a schematical representation of reaction scheme B according to another embodiment of the invention. The partial oxidation reactor 21 containing the first catalyst (CAT-A) converts fresh and recycled ethane or ethane/ethylene with oxygen into ethylene, acetic acid and carbon dioxide. The effluent of reactor 21 is fed to VAM reactor 23 containing the VAM catalyst (CAT-B) via optional heat exchanger 22, which allows adjustment of the temperature of the feed to VAM reactor 23. Optionally, the two catalysts CAT-A and CAT-B can be in one reactor in the form of a physical mixture or in alternating layer form. Additional amounts of gases to VAM reactor 23, such as ethylene, acetic acid, and oxygen may be added depending upon the process conditions. The effluent from VAM reactor 23 is fed to gas/liquid separation unit 24, where gases including $CO_2$, $C_2H_4$, and $C_2H_6$, are separated from liquid VAM, acetic acid and water. The gas streams from gas/liquid separation unit 24 are recycled via carbon dioxide removal unit 25 to reactor 21. Optionally, the gas streams can also be recycled to reactor 21 without the absorption unit 25, as the catalyst CAT-A in the reactor 21 is not affected by the presence of carbon dioxide. Further, a specific amount of carbon dioxide also enhances the performance of the catalyst CAT-A. Gases are partially purged to control the build of non reacting species in purge unit 27. Liquid stream from separator unit 24 is fed to distillation unit 26 where acetic acid is separated from VAM and water and is optionally recycled to reactor 23 for make up or can be recovered. VAM goes to a recovery unit and $H_2O$ is recycled to reactor unit 21 for enhancement of acetic acid and selectivity.

EXAMPLES

Catalytic oxidation processes using a first catalyst ((a) or (b) or (c) or mixtures thereof) were carried out in a tubular reactor under the following conditions. All experiments were run at the temperatures set forth below ranging from 260° C. to 286° C., at a pressure of about 14 bar (200 psig)

Reaction products were analyzed on-line by gas chromatography. Oxygen, nitrogen and carbon monoxide were analyzed using a 3 mm by 3 mm column of 13×molecular sieve. Carbon dioxide, ethane, ethylene and water were analyzed using a 1.8 m by 3 mm column packed with material sold under the name HAYASEP™Q. Acetic acid was analyzed using a 0.5 m by 3 mm column packed with material sold under the name PORAPACK™ N.

In all cases, the conversion and selectivity calculations were based on the stoichiometry.

Data for the stage I reaction mentioned in the examples is experimental and the production of vinyl acetate (VAM) data in the stage II is calculated based on 92% yield to VAM from ethylene (*Chem. System* 91-10, October 1992).

Example 1

The production of Van from Ethylene:

The first catalyst (catalyst (a)): $MoV_{0.396}Nb_{0.128}Pd_xO_y$ (where x=1.90e-04 and y is based on the co-ordination valence).

Process conditions for stage I reactor: 286° C./14 bar (200 psi).

Process conditions for stage II reactor as described in reference *Chem. System* 91-10, October 1992.

Results Data:

| Compound | Stage I | | Stage II | |
|---|---|---|---|---|
| (g. mol. min.) | Feed | Product | Feed | Product |
| Ethylene | 5.65E-4 | 2.07E-4 | 2.07E-4 | |
| Oxygen | 6.73E-4 | 1.23E-4 | 1.23E-4 | |
| Nitrogen | 2.53E-3 | 2.47E-4 | | |
| Water | 2.23E-5 | 2.13E-4 | | |
| Acetic Acid | | 2.80E-4 | 2.80E-4 | |
| $CO_2$ | | 1.56E-4 | | |
| VAM | | | | 1.90E-4 |

The nitrogen, $CO_2$ and water are diluents in the stage II reaction.

Example 2

The Production of VAN from Ethane

First catalyst (catalyst (a)): $MoV_{0.396}Nb_{0.128}Pd_xO_y$ (where x is 1.90e-04 and y is based on the co-ordination valence).

Process conditions for stage I reactor: 286° C./14 bar (200 psi).

Process conditions for stage II reactor as described in *Chem. System* 91-10, October 1992.

Results Data:

| Compound | Stage I | | Stage II | |
|---|---|---|---|---|
| (g. mol. min.) | Feed | Product | Feed | Product |
| Ethane | 4.43E-04 | 2.40E-4 | | |
| Oxygen | 5.10E-04 | 5.07E-05 | 5.07E-05 | |
| Nitrogen | 1.92E-03 | 1.98E-03 | | |
| Water | | 3.18E-04 | | |
| Ethylene | | 8.86E-05 | 8.86E-05 | |
| Acetic Acid | | 9.28E-05 | 9.28E-05 | |
| $CO_2$ | | 1.77E-04 | | |
| VAM | | | | 9.00E-5 |

The nitrogen, $CO_2$ and water act as diluents in stage II.

Example 3

The Production of VAX from Ethane

First catalyst (catalyst (a)): $Mo_{2.5}V_{1.0}Nb_{0.32}Pd_{0.03}O_y$ (where y is based on the coordination valence).

Process conditions for stage I reactor: 286° C./14 bar (200 psi) Process conditions for stage II reactor as described in *chem. Systm* 91-10, October 1992.

Results Data:

| Compound | Stage I | | Stage II | |
|---|---|---|---|---|
| (g. mol. min.) | Feed | Product | Feed | Product |
| Ethane | 1.91E-04 | 7.87E-05 | | |
| Oxygen | 2.25E-04 | 1.30E-05 | 5.07E-5 | |
| Nitrogen | 8.45E-04 | 8.40E-04 | | |
| Water | | 1.87E-04 | | |
| Ethylene | | 3.41E-05 | 3.41E-05 | |
| Acetic Acid | | 4.08E-05 | 4.08E-05 | |
| $CO_2$ | | 3.53E-05 | | |
| CO | | 4.68E-05 | | |
| VAM | | | | 3.13E-5 |

The nitrogen, $CO_2$ and water act as diluents in stage II.
Based on the above-described catalytic data, the follow ing general characteristics can be concluded for the methods of the invention:

1. The catalytic methods used show high selectivity to vinyl acetate by oxidizing mixtures of ethane and ethylene.
2. The catalytic methods used also show high selectivity to vinyl acetate by oxidizing ethane.
3. The catalytic method systems used produce vinyl acetate without the production of by-products such as carbon monoxide. This advantage reduces the step of CO conversion to $CO_2$ in the conventional VAM process.

What is claimed is:

1. A process for the production of vinyl acetate monomer comprising the steps of:

(1) contacting a gaseous feed mixture of ethane or ethylene or ethane/ethylene, steam and a molecular oxygen containing gas in the presence of a first catalyst active for oxidation of ethane, ethylene or ethane/ethylene to produce a selective stream of acetic acid, ethylene, carbon dioxide and water and (2) converting a second feed mixture comprising ethylene, acetic acid and oxygen to vinyl acetate monomer in the presence of a second catalyst active for the production of vinyl acetate, wherein said process does not include an intermediate separation step to remove the CO between the two reaction steps characterized by using a first oxidation catalyst selected from the following catalyst compositions:

a catalyst composition comprising the elements Mo, V, Nb, and Pd, in the form of oxides, in the ratio $Mo_aV_bNb_cPd_d$ wherein:
   a is 1 to 5;
   b is 0 to 0.5;
   c is 0.01 to 0.5; and
   d is >0 to 0.2;

a, b, c, d, represent the relative gram-atom ratios of the elements Mo, V, Nb, and Pd respectively in the catalyst or a catalyst composition comprising the elements Mo, V, Pd, Nb, La and X, in the form of oxides, wherein X is Al, Ga, Si or Ge, in the ratio $Mo_aV_bLa_cPd_dNb_eX_f$, wherein:
   a is 1;
   b is 0.01 to 0.9;
   c is >0 to 0.2;
   d is >0 to 0.2;
   e is >0 to 0.2;
   f is >0 to 0.3;

a, b, c, d, e, f represent the relative gram-atom ratios of the elements Mo, V, La, Pd, Nb, and X respectively in the catalyst or a catalyst composition comprising the elements Mo, V, Nb and X (where X is P, B, Hf, Te, As or mixtures thereof) in the form of an oxide, in the following ratio $Mo_aV_bNb_cX_d$ wherein:
   a is 1 to 5;
   b is >0 to 0.1;
   c is 0.01 to 0.5;
   d is >0 to 0.1;

a, b, c, d represent the relative gram-atom ratios of the elements Mo, V, Nb, and X respectively in the catalyst or a mixture between the two previous first oxidation catalysts and a catalyst composition comprising the elements Mo, V, Nb, and Pd, in the form of oxides, in the ratio $Mo_aV_bNb_cPd_d$ wherein:
   a is 1 to 5;
   b is 0 to 0.5;
   c is 0.01 to 0.5; and
   d is >0 to 0.2;

a, b, c, d represent the relative gram-atom ratios of the elements Mo, V, Nb, and Pd respectively in the catalyst.

2. The process of claim 1, wherein said process produces no carbon monoxide.

3. The process of claim 2, wherein said first catalyst and second catalyst are in the form of a fixed or fluidized bed or a solid moving bed reactor.

4. The process of claim 2, wherein said feed mixture is fed into a second reaction zone.

5. The process of claim 4, wherein the second feed mixture for the second step comprises ethylene, acetic acid, $CO_2$ and oxygen.

6. The process of claim 2, wherein said feed mixture comprises molecular oxygen ranging from 0.1 to 25% by volume of the feed mixture.

7. The process of claim 2, wherein said feed mixture is diluted with $N_2$ in an amount ranging from 5 to 90% by volume.

8. The process of claim 2, wherein said feed mixture is diluted with steam in an amount ranging from 0 to 40% by volume.

9. The process of claim 2, wherein said feed mixture comprises from 1% to 95% by volume of ethane, ethylene or mixtures thereof.

10. The process of claim 2, wherein first step oxidation is achieved at a temperature of from 150 to 450° C., under a pressure of from 1 to 34 bar (15 to 500 psi), and with a contact time between reaction mixture and the catalyst of from 2 to 100 seconds.

11. The process of claim 2, wherein said contacting comprises reacting ethane/ethylene with steam and oxygen or a compound capable of providing oxygen in the presence of said first catalyst in a first reaction zone to form a first product mixture comprising ethylene, oxygen, steam and acetic acid and.the said first product mixture is fed into a second reaction zone wherein the ethylene and acetic acid react to form vinyl acetate in the presence of said second reaction catalyst.

12. The process of claim 11, wherein said first product mixture is fed directly into said second reaction zone without adding additional components.

13. The process of claim 11, wherein said first product mixture is fed into said second reaction zone with addition/adjustment of ethylene, acetic acid, oxygen or combinations thereof.

14. The process of claim 11, wherein said first product mixture is subjected to temperature and/or pressure adjustments prior to being fed into said second reaction zone.

15. A process of producing vinyl acetate monomer comprising the step of catalytically oxidizing ethane to form vinyl acetate in a single reaction zone containing a first catalyst having activity for oxidation or ethane to ethylene and acetic acid and a second catalyst having activity for oxidation of ethylene with acetic acid to vinyl acetate, characterized in that said first catalyst is at least one catalyst selected from the following catalyst compositions:

a catalyst composition comprising the elements Mo, V, Pd, Nb, La and X, in the form of oxides, wherein X is Al, Ga, Si or Ge, in the ratio $MO_a.V_b\ La_c, Pd_dNb_eX_f$, wherein:
   a is 1;
   b is 0.01 to 0.9;
   c is >0 to 0.2;
   d is >0 to 0.2;
   e is >0 to 0.2;
   f is >0 to 0.3;

a, b, c, d, e, f represent the relative gram-atom ratios of the elements Mo, V, La, Pd, Nb, and X respectively in the catalyst or a catalyst composition comprising the elements Mo, V, Nb and X (where X is P, B, Hf, Te, As or mixtures thereof) in the form of an oxide, in the following ratio $MO_aV_bNb_cX_d$ wherein:

a is 1 to 5;
b is >0 to 0.1;
c is 0.01 to 0.5;
d is 0 to 0.1;

a, b, c, d represent the relative gram-atom ratios of the elements Mo, V, Nb, and X respectively in the catalyst or a mixture between the two previous first oxidation catalysts and a catalyst composition comprising the elements Mo, V, Nb, and Pd, in the form of oxides, in the ratio $Mo_a.V_bNb_cPd_d$ wherein:

a is 1 to 5;
b is 0 to 0.5;
c is 0.01 to 0.5; and
d is >0 to 0.2;

a, b, c, d represent the relative gram-atom ratios of the elements Mo, V, Nb, and Pd respectively in the catalyst.

* * * * *

UNITED STATES PATENT AND TRADEMARK OFFICE
CERTIFICATE OF CORRECTION

PATENT NO. : 6,605,739 B1
DATED : August 12, 2003
INVENTOR(S) : Karim et al.

It is certified that error appears in the above-identified patent and that said Letters Patent is hereby corrected as shown below:

<u>Title page,</u>
Item [22], after "PCT Filed: May 9, 2000", please add:

-- [30] Priority Data
   May 14, 1999 [US]    United States .........09/312,683 --

Signed and Sealed this

Seventeenth Day of February, 2004

JON W. DUDAS
*Acting Director of the United States Patent and Trademark Office*